United States Patent
Smits

(10) Patent No.: US 6,368,297 B1
(45) Date of Patent: Apr. 9, 2002

(54) HYPEREXTENSION KNEE ORTHOSIS

(75) Inventor: Jan F.A. Smits, Helmond (NL)

(73) Assignee: Camp Scandinavia AB, Helsingborg (SE)

( * ) Notice: Subject to any disclaimer, the term of this patent is extended or adjusted under 35 U.S.C. 154(b) by 0 days.

(21) Appl. No.: 09/402,073

(22) PCT Filed: Mar. 24, 1998

(86) PCT No.: PCT/SE98/00532

§ 371 Date: Oct. 22, 1999

§ 102(e) Date: Oct. 22, 1999

(87) PCT Pub. No.: WO98/43561

PCT Pub. Date: Oct. 8, 1998

(30) Foreign Application Priority Data

Apr. 1, 1997 (SE) .............................................. 9701172

(51) Int. Cl.⁷ .................................................. A61F 5/00
(52) U.S. Cl. ........................................... 602/26; 602/23
(58) Field of Search ............................... 602/5, 16, 26, 602/23, 20, 60–62; 128/882; 623/39

(56) References Cited

U.S. PATENT DOCUMENTS

| | | | |
|---|---|---|---|
| 3,026,869 A | * | 3/1962 | Peach |
| 4,556,053 A | | 12/1985 | Trons |
| 4,633,867 A | | 1/1987 | Kausek |
| 4,697,583 A | * | 10/1987 | Mason et al. ................. 128/80 |
| 4,715,363 A | | 12/1987 | Detty |
| 4,817,588 A | * | 4/1989 | Bledsoe ....................... 128/80 |
| 5,133,341 A | * | 7/1992 | Singer et al. |
| 5,267,946 A | * | 12/1993 | Singer et al. |
| 5,277,698 A | | 1/1994 | Taylor |
| 5,344,390 A | * | 9/1994 | Motloch |
| 5,358,469 A | * | 10/1994 | Patchel et al. ................. 602/5 |
| 5,810,752 A | * | 9/1998 | Grifka |

FOREIGN PATENT DOCUMENTS

DE 2426079 12/1974

* cited by examiner

*Primary Examiner*—Denise Pothier
(74) *Attorney, Agent, or Firm*—Ladas & Parry

(57) ABSTRACT

A knee orthosis to prevent hyperextension having a top portion secured to a patient's thigh, a lower portion secured to the patient's lower leg and a joint portion. A connection bar of variable width connects the two hinges of the joint portion in or near the popliteal space of the patient. The connection bar, the top portion and the lower portion include stop surfaces, which inhibit hyperextension of the patient's knee beyond a first predetermined angle and which inhibits bending of the patient's knee to less than a second predetermined angle. In addition, the top and lower portions include brace members having ventral and dorsal slits vertically offset from each other in order to produce a torquing action on the brace.

18 Claims, 2 Drawing Sheets

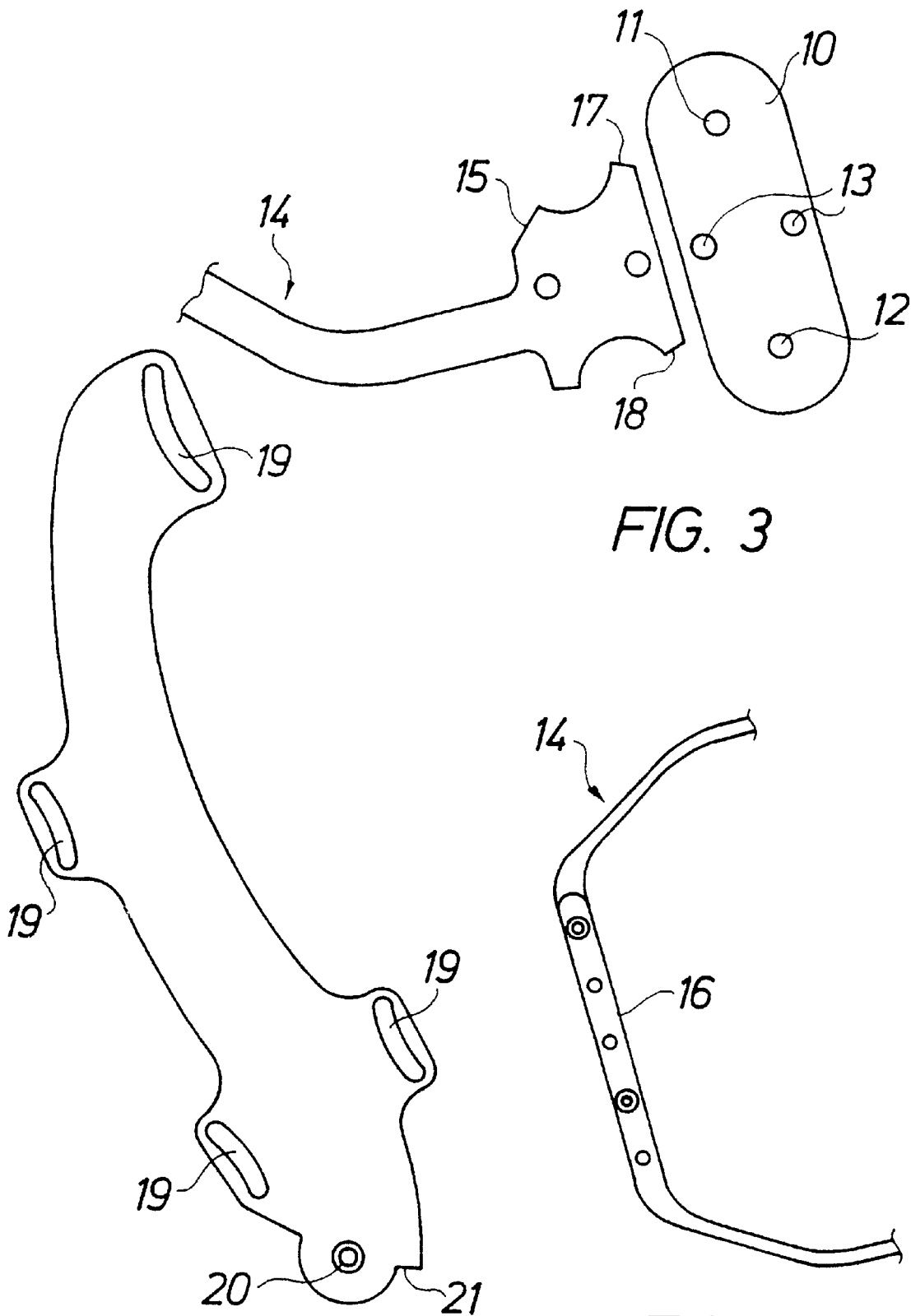

HYPEREXTENSION KNEE ORTHOSIS

FIELD OF THE INVENTION

The present invention relates to a knee orthosis preventing hyperextension, i.e. excessive extension of the knee joint. The orthosis features a two-axes joint allowing a natural joint motion and a popliteal connection bar providing the required stability. The orthosis is light-weight and made of few components. The orthosis allows easy donning and doffing by incorporating adequate straps.

STATE OF THE ART

The first version of the hyperextension orthosis consisted of a rigid brace without any hinge of joint. Thus, it did not bend with the leg which, of course, was impractical. This orthosis was replaced by an orthosis having a single axis joint. Even though this was an improvement over the rigid brace, the single axis joint did not follow the natural motion of the knee joint. The orthosis was provided with a stabilizing connection bar in the popliteal space. When the patient bent the knee joint, the leg pinched around the connection bar. Thus, the movement of the patient's leg was limited and experienced as uncomfortable. Furthermore, the orthosis was secured to the leg by ventral and dorsal straps attached to the orthosis at the same height. Due to this arrangement, the orthosis was subject to slipping down the leg.

The present invention solves the problems stated above by providing a knee orthosis comprising a two-axes joint promoting a natural motion. Also, the ventral and dorsal straps are arranged at different heights and preferably offset from a centre line. This arrangement distributes the forces and torques on the orthosis in an advantageous manner preventing slipping.

SUMMARY OF THE INVENTION

Thus, the present invention provides a knee orthosis comprising a top portion to be secured at the patient's thigh and a lower portion to be secured at the patient's lower leg, a joint portion connecting the top and lower portions, and strap means for securing the orthosis. According to the invention the joint portion has two axes preventing hyperextension but otherwise allowing a free motion of the patient's leg.

Preferably, the joint portion comprises two hinges connected together by a connection bar positioned in or near the popliteal space.

In a preferred embodiment, the top and lower portions comprise brace members having ventral and dorsal slits for the strap means. The ventral and dorsal slits are positioned at different heights and may be offset from the centre line of the orthosis.

The invention is set forth in greater detail in the accompanying claims.

BRIEF DESCRIPTION OF THE DRAWINGS

The invention will be explained further in detail with reference to the accompanying drawings in which:

FIG. 2 is a detail view of a brace member of the orthosis of FIG. 1, FIG. 3 is a side view of a joint plate and a hinge end of connection bar, and FIG. 4 is a top view of a portion of a connection bar of the present invention.

DETAILED DESCRIPTION OF PREFERRED EMBODIMENTS

Figure 1:
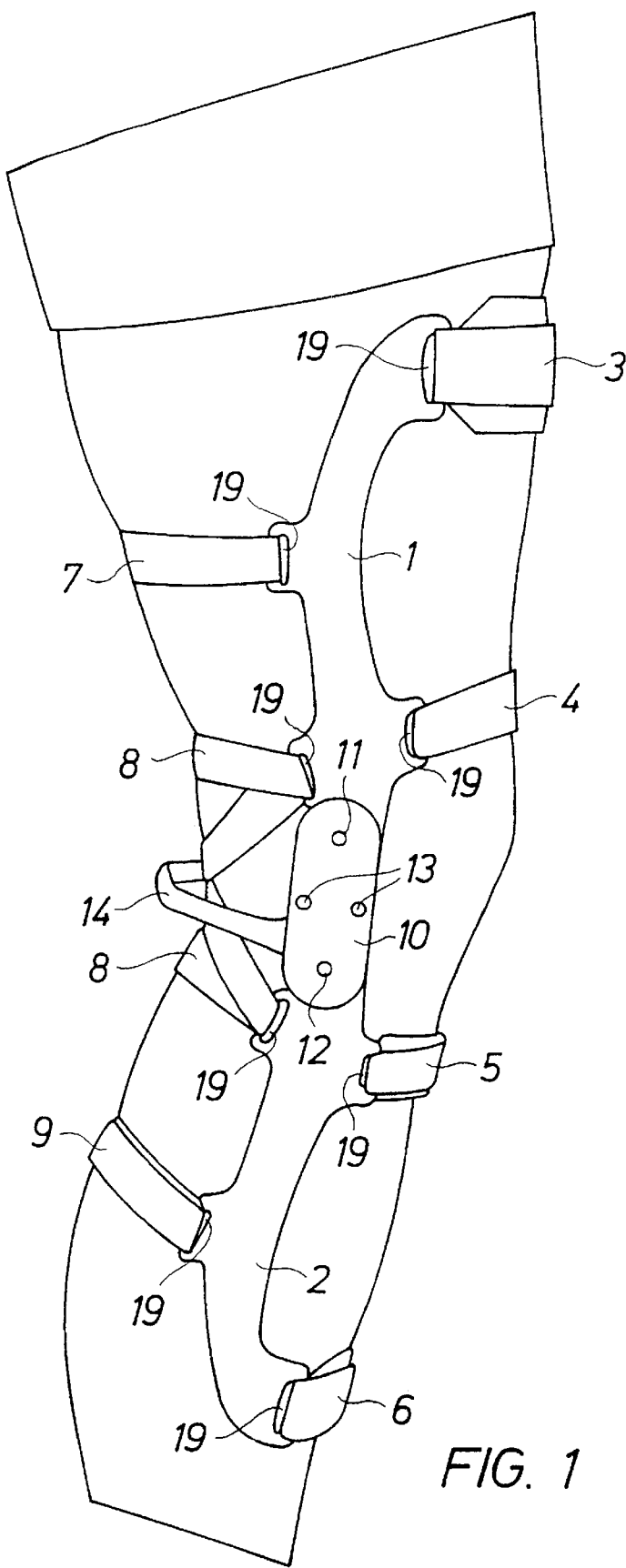
FIG. 1 is a side view of a knee joint orthosis according to the present invention secured the leg of a patient.

As is mentioned in the introduction, the present invention relates to a hyperextension knee joint orthosis, i.e. an orthosis preventing excessive extension of the knee joint. Indications are a generally weak knee joint with instable knee, especially in case of hyperextension caused by laxity of the ligaments, and genu valgum or genu varum.

With reference to FIG. 1, the knee orthosis generally consists of a top portion and a lower portion connected by a joint portion. The top portion comprises brace members 1 and two ventral straps 3 and 4 and two dorsal straps 7 and 8. Similarly, the lower portion comprises brace members 2 and two ventral straps 5 and 6 as well as two dorsal straps 8 and 9. Conveniently, as is shown, the lower dorsal strap of the top portion and the top dorsal strap of the lower portion consists of the same strap 8 which is passed through slits 19 and in a cross at the back of the knee, i.e. in the popliteal space. The joint portion comprises a joint plate 10 and a connection bar 14.

Only one side of the orthosis and the leg is shown but it will be understood that the orthosis comprises the identical corresponding parts at the other side. Besides, one and the same orthosis may easily be adapted for the right or the left leg of a patient.

One brace member is shown in detail in FIG. 2. All four brace members are preferably identical in shape. As may be seen, slits 19 are provided for the various straps. Also the brace member has a pivot 20 to provide a pivot axis of the joint together with the joint plate 10.

In FIG. 3, the joint plate 10 is shown to the right, while the hinge end 15 of the connection bar 14 is shown to the left. The joint plate 10 provides a top axis 11 and a lower axis 12 together with the respective brace members 1 and 2. The axes are spaced by approximately 50 mm. The distance is not very critical. Inside the joint plate, the end portion 15 of the connection bar is attached by rivers 13 or the like. The end portion 5 constitutes a stop portion governing the motion of the brace members 1 and 2. The stop portion has a first top stop surface 17 and a first lower stop surface 18 which engage corresponding second stop surfaces 21 (FIG. 2) on the brace members. Except for the stop thus provided, the top and lower brace members 1, 2 can move freely and independently of each other. The engagement of the first and second stop surfaces inhibits hyperextension beyond a first predetermined angle and inhibits bending of the patient's leg to less than a second predetermined angle.

The orthosis allows a full extension of approximately 170° and a bending of the leg to a full contraction at approximately 15°. It will be appreciated by persons skilled in the art that full extension angles greater or less than 170° easily may be obtained by adapting the stop surfaces 17, 18, 21. Also, at full contraction, often the muscle of the patient's legs prevent further contraction. The sole desired function of the orthosis is to prevent hyperextension and the other extreme of the leg bending movement is not of particular interest but the orthosis should only follow the natural movement of the knee joint as close as possible, such that the patient does not experience any discomfort or resistance except at the extension stop.

For a correct operation of the joint portion the joint plates 10 are connected by a connection bar 14 maintaining the two joint plates (of which only one is shown in FIG. 1) in parallel. The connection bar consists of two hinge portions 15, as is described above, and a popliteal stabilizing bar 16. The popliteal bar consists of a flat portion that is angled relative to the vertical. This is to increase the stabilizing effect and strength of the bar. It is also more comfortable when the patient bends his leg around the connection bar 14 in that no edges of the connection bar are pressed into the leg.

It is advantageous that the connection bar 14 has a variable width so that the orthosis fits different widths of legs. An adjustable variable width of approximately 10–14.5 cm accommodates the majority of the grown up population. In FIG. 4 the connection bar 14 comprises two parts sliding along each other but other arrangements are evident to a person skilled in the art. The connection bar 14 is secured by connecting screws. The most adequate way for this connecting bar is to use two screws to secure the width and stability of the medial and lateral joint.

As is mentioned previously, the orthosis has three dorsal straps 7, 8, 9. These straps do not have to be removed for donning and doffing the orthosis. The dorsal straps will be adjustable for circumference by means of pile and loop connections (e.g. VELCRO® tapes). On the other hand, the ventral straps 3, 4, 5, 6 are provided with pile and loop connections or the like to be easily opened and removed and put back on again. In the illustrated embodiment of the orthosis, four ventral straps are provided but, in fact, only three straps are needed and the ventral strap 4 above the knee is not strictly needed for securing the orthosis but gives the patient a comfortable feel.

The slits 19 for the ventral and dorsal straps are advantageously arranged at different heights, the top ventral strap 3 and lower ventral strap 6 being at the highest and lowest positions, respectively. The slits 19 are also offset from a vertical centre line of the orthosis. This arrangement results in that the forces applied by the straps and acting at the slits 19 produce torques acting on the brace members. These torques assist in holding the orthosis to the led in a way which were not possible if the slits 19 were arranged at the same height. In a relaxed position the distal part of strap 8 and strap 5 produce a ring around the smallest circumference of the leg, namely over the Gastrocnemius. Thus, the orthosis is prevented from slipping down the patient's leg and the weight of the orthosis rests mainly on the large calf muscle (*M. Gastrocnemius*).

As is indicated above, all the brace members are made from identical plates having the same punched holes. Thus, the number of components to be manufactured is kept as low as possible. The brace members are preferably produced from a 2 mm aluminium sheet providing the required strength and low weight. The brace members may be bent manually, or with a tool, to adapt the orthosis to the patient's leg, the top brace members 1 usually being bent outwards to accommodate the relatively thicker thigh and the low members 2 being bent inwards, or contoured after the dimension of the leg, if necessary.

All the hinges of the orthosis may be produced from a 2 mm aluminium sheet. However, it is preferred that the connection bars 14 and the joint plates 10 are made of stainless steel because of its greater strength.

Thus, the present hyperextension knee orthosis presents several advantages over the prior art orthosis. The two-axes joint portion allows for a free joint motion of 170° to 15° while following the natural movement of the patientxs knee joint as close as possible. The incorporated straps make handling easier. The orthosis has a slim design and is light-weight (approximately 300 g). The orthosis does not migrate (slip) because of the adequate positioning of the straps. The popliteal connection bar keeps the essential parts in parallel.

While the invention has been set forth in great detail, it is appreciated by persons skilled in the art that the orthosis may be subject to various modifications and rearrangements without departing from the scope of the invention which is defined in the accompanying claims.

What is claimed is:

1. A knee orthosis comprising a top portion to be secured at a patient's thigh and a lower portion to be secured at the patient's lower leg, a joint portion connecting the top and lower portions, and strap means for securing the orthosis, wherein the joint portion has two axes and prevents hyperextension, and wherein the joint portion comprises two hinges connected together by a connection bar positionable in or near the popliteal space, said connection bar having at least one first stop surface, wherein said top portion and lower portion each comprise a brace member, said brace members each having at least one second stop surface which engages said at least one first stop surface of said connection bar to inhibit hyperextension beyond a first predetermined angle and to inhibit bending of the leg to less than a second predetermined angle, said brace members further having ventral slits and dorsal slits for receiving said strap means and, at least one of said ventral slits being positioned at a different height relative to one of said dorsal slits, so that said strap means connecting said brace members exert forces thereon, producing torque acting on said brace members.

2. A knee orthosis according to claim 1, wherein the two axes are spaced by a distance of approximately 50 mm.

3. A knee orthosis according to claim 1, wherein the connection bar has a variable width.

4. A knee orthosis according to claim 1, wherein the ventral and dorsal slits are offset from a center line of the orthosis.

5. A knee orthosis according to claim 1, wherein the brace members are identical in shape for the top and lower portions.

6. A knee orthosis according to claim 1, wherein the brace members are shaped to be adapted to the shape of the patient's leg.

7. A knee orthosis according to claim 1, wherein the top and lower portions and the joint portion are made of aluminum.

8. A knee orthosis according to claim 1, wherein the connection bar is made of steel.

9. A knee orthosis according to claim 1, wherein the brace member of the top portion further comprises a top ventral slit, a top dorsal slit, a bottom ventral slit and a bottom dorsal slit, said top ventral slit is disposed higher than said top dorsal slit in each brace member, and said bottom ventral slit is disposed lower than said bottom dorsal slit in each brace member.

10. A knee orthosis according to claim 1, wherein the brace members are connected to the joint portion at said hinges so that each brace member can move freely and independently of the other.

11. A knee orthosis comprising a top portion to be secured at a patient's thigh and a lower portion to be secured at the patient's lower leg, a joint portion comprising two hinges connecting the top and lower portions, and a strap means for securing the orthosis, the joint portion having two axes defined by and disposed at said two hinges, said two hinges being connected to each other by a connection bar positionable in or near the popliteal space, said connection bar having at least one first stop surface, and said strap means further comprising at least two dorsal strap sections passed through slits in said top and lower portions, each of said top and lower portions having at least one second stop surface which engages said connection bar at least one first stop surface to inhibit hyperextension beyond a first predetermined angle and to inhibit bending of the leg to less than a second predetermined angle, wherein said at least two dorsal strap sections cross over each other adjacent the popliteal space during use so as to prevent hyperextension.

12. A knee orthosis according to claim 11 wherein said top and lower portions each further comprise at least one brace member, said brace members each having a plurality of dorsal slits for receiving said dorsal strap sections, said dorsal strap sections passing through said dorsal slits, and dorsal slits being vertically offset from ventral slits, disposed ventrally of the orthosis, and said orthosis including ventral strap means having at least one ventral strap, so that the forces applied by the strap means at the slits produce torque acting on said brace members.

13. A knee orthosis according to claim 12 wherein the ventral and dorsal slits are offset from a center line of orthosis.

14. A knee orthosis according to claim 12, wherein the brace members are identical in shape for the top and lower portions.

15. A knee orthosis according to claim 12, wherein the at least one brace member of the top portion further comprises a top ventral slit, a top dorsal slit, a bottom ventral slit and a bottom dorsal slit, and said top ventrical slit is disposed higher than said top dorsal slit in each brace member, and said bottom ventral slit is disposed lower than said bottom dorsal slit in each brace member.

16. A knee orthosis according to claim 11, wherein the top and lower portions and the joint portion are made of aluminum.

17. A knee orthosis according to claim 11, wherein the connection bar is made of steel.

18. A knee orthosis according to claim 11, wherein the connection bar has a variable width.

* * * * *